United States Patent

Boshagen et al.

Patent Number: 5,015,657
Date of Patent: May 14, 1991

[54] 2-HALOGEN-SUBSTITUTED N-INDOLYLETHYL-SULPHONAMIDES AND INHIBITING PLATELET AGGREGATION AND ANTOGONIZING THROMBOXANE A₂ THERE WITH

[75] Inventors: Horst Boshagen, Haan; Elisabeth Perzborn, Wuppertal; Volker-Bernd Fiedler, Leverkusen, all of Fed. Rep. of Germany

[73] Assignee: Bayer Aktiengesellschaft, Leverkusen, Fed. Rep. of Germany

[21] Appl. No.: 436,858

[22] Filed: Nov. 15, 1989

[30] Foreign Application Priority Data

Nov. 30, 1988 [DE] Fed. Rep. of Germany ....... 3840338

[51] Int. Cl.⁵ .................. C07D 209/18; A61K 31/405
[52] U.S. Cl. ........................... 514/419; 548/494
[58] Field of Search ................... 548/494; 514/419

[56] References Cited

FOREIGN PATENT DOCUMENTS 3514696 11/1986 Fed. Rep. of Germany .
3613623 10/1987 Fed. Rep. of Germany .

Primary Examiner—David B. Springer
Attorney, Agent, or Firm—Sprung Horn Kramer & Woods

[57] ABSTRACT

Inhibiting platelet aggregation and antagonizing thromboxane A₂ with new 2-halogen-substituted N-indolyethyl-sulphonamides of the formula

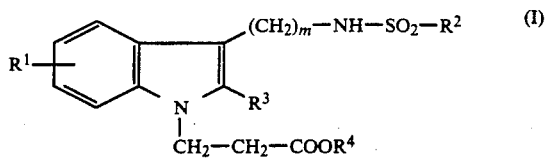

in which
$R^1$ represents hydrogen, halogen, trifluoromethyl, carboxyl or alkoxycarbonyl having up to 8 carbon atoms, or
represents straight-chain or branched alkyl having up to 8 carbon atoms, or represents cycloalkyl having 3 to 8 carbon atoms, which is optionally substituted by carboxyl, halogen, alkoxy or alkoxycarbonyl having in each case up to 8 carbon atoms, cyano or hydroxyl, or
represents a group of the formula $-S(O)_n-R^5-$, $-NR^6R^7$ or $-OR^8$
represents straight-chain or branched alkyl having up to 10 carbon atoms, which is optionally substituted by halogen, phenyl, hydroxyl or cyano, or
represents aryl having 6 to 10 carbon atoms, which is optionally substituted by up to 5 identical or different substituents from the group comprising halogen, cyano, trifluoromethyl, trifluoromethoxy, trifluoromethylthio, alkyl, alkoxy, alkoxycarbonyl or alkylthio having in each case up to 8 carbon atoms, hydroxyl, carboxyl, phenyl, phenoxy, benzyloxy and benzylthio, or by a group of the formula $-NR^6R^7$,
$R^3$ represents halogen,
$R^4$ represents hydrogen or straight-chain or branched alkyl having up to 8 carbon atoms, or represents phenyl
and
m represents one of the numbers 2, 3 or 4, and salts thereof.

13 Claims, No Drawings

2-HALOGEN-SUBSTITUTED N-INDOLYLETHYL-SULPHONAMIDES AND INHIBITING PLATELET AGGREGATION AND ANTOGONIZING THROMBOXANE A₂ THERE WITH

The invention relates to new 2-halogen-substituted N-indolylethyl-sulphonamides, processes for their preparation and their use in medicaments.

It is known that N-indolylethyl-sulphonamides and N-dihydroindolylethyl-sulphonamides have a platelet aggregation-inhibiting and thromboxane $A_2$-antagonistic action [compare DOS (German Published Specification) 3,514,696 and DOS (German Published Specification) 3,613,623].

New 2-halogenated N-indolylethyl-sulphonamides of the general formula (I)

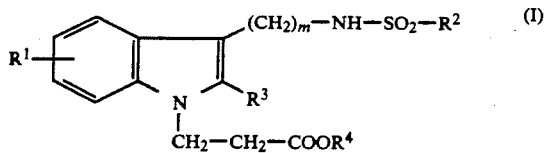

in which
R¹ represents hydrogen, halogen, trifluoromethyl, carboxyl or alkoxycarbonyl having up to 8 carbon atoms, or
represents straight-chain or branched alkyl having up to 8 carbon atoms, or represents cycloalkyl having 3 to 8 carbon atoms, which is optionally substituted by carboxyl, halogen, alkoxy or alkoxycarbonyl having in each case up to 8 carbon atoms, cyano or hydroxyl, or
represents a group of the formula $-S(O)_n-R^5$, $-NR^6R^7$ or $-OR^8$
wherein
R⁵ denotes straight-chain or branched alkyl having up to 8 carbon atoms or aryl having 6 to 10 carbon atoms,
R⁶ and R⁷ are identical or different and denote hydrogen, straight-chain or branched alkyl having up to 8 carbon atoms, aryl having 6 to 10 carbon atoms or acetyl,
R⁸ denotes hydrogen, straight-chain or branched alkyl or alkylsulphonyl having up to 8 carbon atoms, aryl or arylsulphonyl having in each case 6 to 10 carbon atoms or trifluoromethyl,
and
n denotes the number 0, 1 or 2,
R² represents straight-chain or branched alkyl having up to 10 carbon atoms, which is optionally substituted by halogen, phenyl, hydroxyl or cyano, or
represents aryl having 6 to 10 carbon atoms, which is optionally substituted by up to 5 identical or different substituents from the group comprising halogen, cyano, trifluoromethyl, trifluoromethoxy, trifluoromethylthio, alkyl, alkoxy, alkoxycarbonyl or alkylthio having in each case up to 8 carbon atoms, hydroxyl, carboxyl, phenyl, phenoxy, benzyloxy and benzylthio, or by a group of the formula $-NR^6R^7$, wherein
R⁶ and R⁷ have the abovementioned meanings,
R³ represents halogen,
R⁴ represents hydrogen or straight-chain or branched alkyl having up to 8 carbon atoms, or represents phenyl, or represents amino
and
m represents one of the numbers 2, 3 or 4, and salts thereof, have now been found.

The 2-halogen-substituted N-indolylethyl-sulphonamides according to the invention can also exist in the form of their salts. Salts with organic or inorganic bases may be mentioned in general here.

In the context of the present invention, physiologically acceptable salts are preferred. Physiologically acceptable salts of the 2-halogen-substituted N-indolylethyl-sulphonamides can be metal or ammonium salts of the substances according to the invention which have a free carboxyl group. Particularly preferred salts are, for example, sodium, potassium, magnesium or calcium salts, and ammonium salts which are derived from ammonia or organic amines, such as, for example, ethylamine, di- or triethylamine, di- or triethanolamine, dicyclohexylamine, dimethylaminoethanol, arginine or ethylenediamine.

Surprisingly, the substances according to the invention exhibit a platelet aggregation-inhibiting and a thromboxane $A_2$-antagonistic action and can be used for the therapeutic treatment of humans and animals.

Preferred compounds are those of the general formula (I) in which
R¹ represents hydrogen, fluorine, chlorine, bromine, trifluoromethyl, carboxyl or alkoxycarbonyl having up to 6 carbon atoms, or
represents straight-chain or branched alkyl having up to 6 carbon atoms, or represents cycloalkyl having 3 to 6 carbon atoms, which is optionally substituted by carboxyl, fluorine, chlorine, bromine, alkoxy or alkoxycarbonyl having in each case up to 6 carbon atoms, cyano or hydroxyl, or
represents a group of the formula $-S(O)_n-R^5$, $-NR^6R^7$ or $-OR^8$,
wherein
R⁵ denotes straight-chain or branched alkyl having up to 6 carbon atoms or phenyl,
R⁶ and R⁷ are identical or different and denote hydrogen, straight-chain or branched alkyl having up to 6 carbon atoms, phenyl or acetyl,
R⁸ denotes hydrogen, straight-chain or branched alkyl or alkylsulphonyl having in each case up to 6 carbon atoms, phenyl or trifluoromethyl,
and
n denotes the number 0, 1 or 2,
R² represents straight-chain or branched alkyl having up to 8 carbon atoms, which is optionally substituted by fluorine, chlorine, bromine, phenyl, hydroxyl or cyano, or
represents phenyl, which is optionally substituted by up to 3 identical or different substituents from the group comprising fluorine, chlorine, bromine, cyano, trifluoromethyl, trifluoromethoxy, trifluoromethylthio, alkyl, alkoxy, alkoxycarbonyl or alkylthio having in each case up to 6 carbon atoms, hydroxyl, carboxyl, phenyl, phenoxy, benzyloxy and benzylthio or by a group of the formula $-NR^6R^7$, wherein
R⁶ and R⁷ have the abovementioned meanings,
R³ represents fluorine, chlorine, bromine or iodine,
R⁴ represents hydrogen or straight-chain or branched alkyl having up to 6 carbon atoms, or represents phenyl and m represents one of the numbers 2 or 3, and salts thereof.

Particularly preferred compounds are those of the general formula (I) in which $R^1$ represents hydrogen, fluorine, chlorine or trifluoromethyl, or represents methyl, ethyl or propyl, or represents a group of the formula $-NR^6R^7$ or $-OR^8$, wherein $R^6$ and $R^7$ are identical or different and denote hydrogen, methyl, ethyl or propyl, and $R^8$ denotes hydrogen, methyl or ethyl, $R^2$ represents methyl, ethyl, propyl, isopropyl, butyl or tert.-butyl, which is optionally substituted by fluorine, chlorine, phenyl, hydroxyl or cyano, or represents phenyl, which is optionally substituted by up to 3 identical or different substituents from the group comprising fluorine, chlorine, bromine, cyano, trifluoromethyl, trifluoromethoxy, trifluoromethylthio, methyl, ethyl, propyl, isopropyl, butyl, tert.-butyl, methoxy, ethoxy, methoxycarbonyl, ethoxycarbonyl, methylthio, ethylthio, hydroxyl, carboxyl, phenyl, phenoxy, benzyloxy and benzylthio, or by a group of the formula $-NR^6R^7$, wherein $R^6$ and $R^7$ have the abovementioned meanings, $R^3$ represents fluorine, chlorine or bromine, $R^4$ represents hydrogen, straight-chain or branched alkyl having up to 4 carbon atoms or phenyl and m represents the number 2, and salts thereof.

A process has furthermore been found for the preparation of the compounds of the general formula (I) according to the invention, which is characterized in that indoles of the general formula (II)

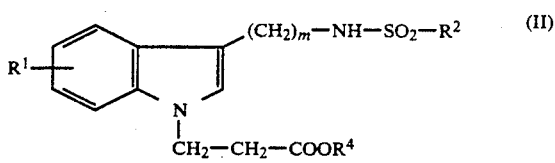

in which $R^1$, $R^2$, $R^4$ and m have the abovementioned meanings, are reacted with halogen, such as fluorine, chlorine or bromine, and, in the case where $R^4$ represents alkyl or phenyl, the products are hydrolyzed with bases to give the corresponding acids ($R^4$=hydrogen), and in the case where $R^4$ represents amino, the according esters or acids ($R^4$=hydrogen, alkyl or phenyl) are treated with ammonia on usual activated conditions.

The reaction of the indoles of the general formula (II) in which $R^4$ represents alkyl if preferred.

The indoles of the general formula (II) are known in most cases [compare DOS (German Published Specification) 3,514,696], or they can be prepared by the method described in DOS (German Published Specification) 3,613,623.

The process stages according to the invention can be illustrated by the following equations:

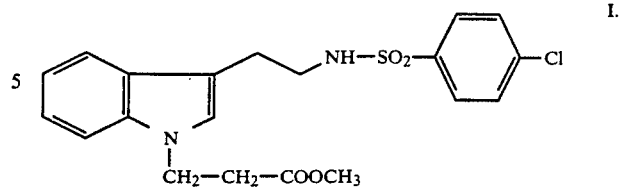

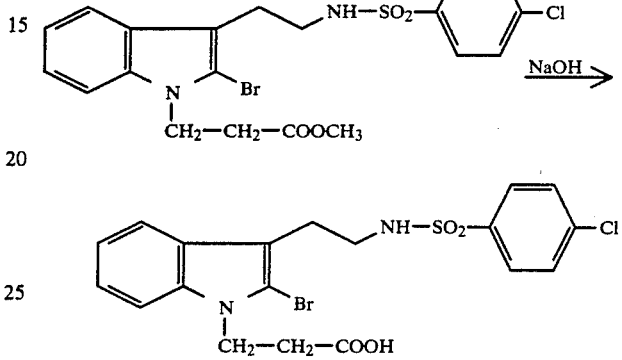

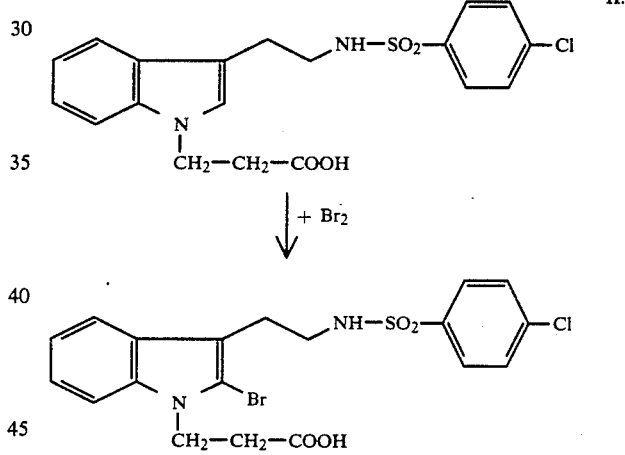

Solvents for the process stages according to the invention can be inert organic solvents which do not change under the reaction conditions. These include, preferably, hydrocarbons, such as benzene, toluene, xylene, cyclohexane, hexane or petroleum fractions, chlorohydrocarbons, such as methylene chloride or chloroform, dimethylformamide or dimethyl sulphoxide.

The halogenation is in general carried out in a temperature range from $-20°$ C. to $+30°$ C., preferably from $-10°$ C. to $0°$ C.

In general, 1 to 20 mols, preferably 1 to 10 mols, of halogen are employed per mol of the indoles of the general formula (II).

The process stages according to the invention are in general carried out under normal pressure. However, it is also possible for the processes to be carried out under reduced pressure or increased pressure (for example in a pressure range from 0.5 to 5 bar).

The hydrolysis of the compounds of the general formula (I) in which $R^4$ represents alkyl or phenyl to give the corresponding acids is carried out in a manner which is known per se in the presence of bases, such as alkali metal or alkaline earth metal hydroxides or alkanolates, in solvents, such as water or alcohols. Bases which are preferably employed are sodium hydroxide, potassium hydroxide, barium hydroxide, sodium methanolate, potassium methanolate, sodium ethanolate or potassium ethanolate, preferably in water or methanol, ethanol, propanol or isopropanol or in mixtures of these solvents.

In general, 1 to 100 mols, preferably 2 to 20 mols, of base are employed per mol of the 2-halogen-substituted N-{2-[1-(2-alkoxycarbonylethyl)-1H-indol-3-yl]}ethyl-sulphonamides.

The hydrolysis is carried out in a temperature range from 0° C. to 100° C., preferably from 20° C. to 80° C.

The new 2-halogen-substituted N-indolylethylsulphonamides and salts thereof can be employed as active compounds in medicaments. The active compounds have a platelet aggregation-inhibiting and thromboxane $A_2$-antagonistic action. They can preferably be employed for the treatment of thromboses, thromboembolisms and ischaemias, as antiasthmatics and as antiallergics.

To determine the platelet aggregation-inhibiting action, blood of healthy volunteers of both sexes was used. 9 parts of blood were admixed to one part of 3.8% strength aqueous sodium citrate solution as an anticoagulant. Platelet-rich citrate plasma (PRP) is obtained from this blood by means of centrifugation (Jürgens/Beller, Klinische Methoden der Blutgerinnungsanalyse [Clinical Methods of Blood Coagulation Analysis]; Thieme Verlag, Stuttgart, 1959).

For these investigations, 0.8 ml of PRP and 0.1 ml of the active compound solution were preincubated in a waterbath at 37° C. The platelet aggregation was then determined by the turbidometric method (Born, G. V. R., J. Physiol. (London), 162, 67, 1962) in an aggregometer at 37° C. (Therapeutische Berichte 47, 80–86, 1975). For this, 0.1 ml of collagen, an aggregation-inducing agent, was added to the preincubated sample. The change in optical density in the sample of PRP was recorded over a period of 6 minutes and the deflection after 6 minutes was determined. For this, the percentage inhibition in comparison with the control was calculated. The range of the minimum effective concentration is stated as the limit concentration.

The limit concentrations are between 0.003 and 10 mg/l.

Example 21

EC=0.01–0.03 mg/l.

Example 22

EC=0.03–0.1 mg/l.

The new active compounds can be converted into the customary formulations, such as tablets, capsules, dragees, pills, granules, aerosols, syrups, emulsions, suspensions and solutions, in a manner which is known per se using inert non-toxic pharmaceutically suitable excipients or solvents. The therapeutically active compound here should in each case be present in a concentration of about 0.5 to 90% by weight, preferably 5 to 70% by weight, which is sufficient to achieve the stated dosage range.

The formulations are prepared, for example, by extending the active compounds with solvents and/or excipients, if appropriate using emulsifying agents and/or dispersing agents, and, for example in the case where water is used as the diluent, organic solvents can be used as auxiliary solvents if appropriate.

Examples of auxiliaries which may be mentioned are: water, non-toxic organic solvents, such as paraffins (for example petroleum fractions), vegetable oils (for example groundnut oil/sesame oil), alcohols (for example ethyl alcohol or glycerol) and glycols (for example propylene glycol or propylethylene glycol), solid excipients, such as, for example, natural rock powders (for example kaolins, aluminas, talc or chalk), synthetic rock powders (for example highly disperse silicic acid or silicates), sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium lauryl sulphate).

The administration can be effected in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various additional substances, such as starch, preferably potato starch, gelatine and the like. Lubricants, such as magnesium stearate, sodium lauryl sulphate and talc, can furthermore be co-used for tabletmaking. In the case of aqueous suspensions and/or elixirs intended for oral uses, various flavor-improving agents or dyestuffs can be added to the active compounds in addition to the abovementioned auxiliaries.

In the case of parenteral use, solutions of the active compounds can be employed, using suitable liquid excipients.

In general, it has proved advantageous in the case of intravenous administration to administer amounts of about 0.001 to 1 mg/kg, preferably about 0.01 to 0.5 mg/kg of body weight, in order to achieve effective results. In the case of oral administration, the dosage is in general about 0.01 to 20 mg/kg, preferably 0.1 to 10 mg/kg of body weight.

However, it may be advantageous to deviate from the amounts mentioned, and in particular as a function of the body weight or nature of the administration route, the individual behavior towards the medicament, the nature of its formulation and the time or interval at which administration takes place. Thus, in some cases it may be sufficient to manage with less than the abovementioned minimum amount, whereas in other cases the upper limit mentioned must be exceeded. Where relatively large amounts are administered, it may be advisable to divide these into several individual doses over the day.

Example 1

N-[2-(1H-Indol-3-yl)]ethyl-(4-methylphenyl)sulphonamide

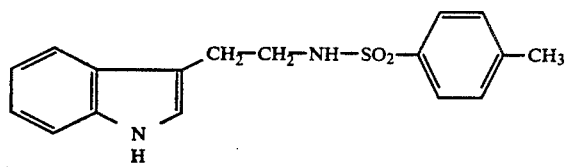

17.5 g (110 mmol) of tryptamine and 18.0 g (220 mmol) of sodium acetate are dissolved in 250 ml of ethanol. 20.97 g (110 mmol) of p-toluenesulphonyl chloride, dissolved in 100 ml of ethanol, are added dropwise at 0° C. The mixture is stirred first at room temperature for 1 hour and then under reflux for 1 hour. Water is subsequently added in an amount such that a clear solution forms. Some of the ethanol is distilled off. The product crystallizes out and is filtered off with suction and recrystallized from isopropanol.

Yield: 20.7 g (60% of theory)
Melting point: 118° C.
$R_f = 0.6$ (toluene:ethanol 3:1)
Thin layer chromatography, aluminum foil, silica gel 60
$F_{254}$, layer thickness 0.2 mm, Art. 5562 Merck

Example 2

N-[2-Cyanoethyl]-N-{2-[1-(2-cyanoethyl)-1H-indol-3-yl]}-ethyl-(4-methylphenyl)sulphonamide

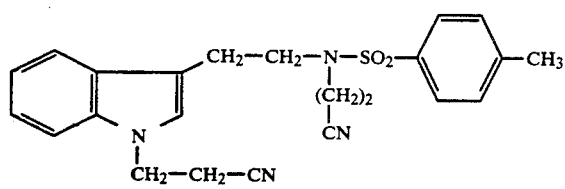

10 g of the compound from Example 1 are dissolved in 150 ml of dioxane. 10 ml of acrylonitrile are then added. 1 ml of benzyltrimethylammonium hydroxide solution (40% strength), dissolved in 4 ml of methanol, is added to this solution. The mixture is stirred at 80° C. for 5 hours and then introduced into water. It is extracted three times with ethyl acetate. The organic phase is washed with water, dried over MgSO$_4$, filtered with suction and concentrated on a rotary evaporator. The product crystallizes out with a little ether. It is recrystallized from ethanol/acetonitrile (1:1).

Yield: 10.1 g (75.5% of theory)
Melting point: 88° C.
$R_f = 0.5$ (toluene:ethanol 3:1)
Thin layer chromatography, aluminum foil, silica gel 60
$F_{254}$, layer thickness 0.2 mm, Art. 5562 Merck

Example 3

N-{2-[1-(2-Carboxyethyl)-1H-indol-3-yl]}ethyl-(4-methylphenyl)sulphonamide

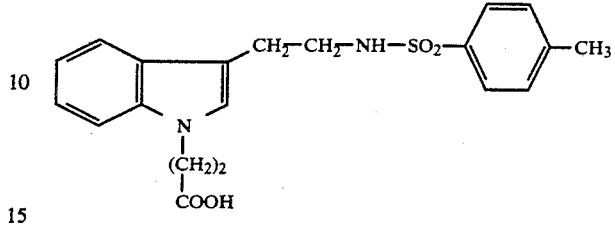

10 g of the compound from Example 2 are stirred under reflux in 300 ml of 10% strength potassium hydroxide solution for 3 hours. The mixture is then rendered acid with 6 molar HCl and extracted three times with chloroform. The organic phase is washed twice with water, dried over MgSO$_4$ and concentrated on a rotary evaporator. The product crystallizes out with a little ethyl acetate and is filtered off with suction.

Yield: 4.7 g (51.1% of theory)
Melting point: 126° C.
$R_f = 0.32$ (toluene:ethanol 3:1)
Thin layer chromatography, aluminum foil, silica gel 60
$F_{254}$, layer thickness 0.2 mm, Art. 5562 Merck

Example 4

N-{2-[1-(2-Methoxycarbonyl-ethyl)-1H-indol-3-yl]}ethyl-(4-methyl-phenyl)sulphonamide

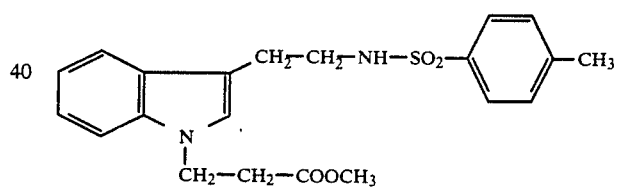

100 g of thionyl chloride are added dropwise to 400 ml of methanol at −20° C., while stirring. When the addition has ended, the mixture is stirred at the same temperature for a further 5 minutes. It is cooled to −50° C. and 20 g (54 mmol) of the compound from Example 3 are added. After the reaction mixture has been stirred at room temperature for 2 hours, it is concentrated on a rotary evaporator. The residue which remains is dissolved in ethyl acetate and the solution is washed in succession with saturated sodium bicarbonate solution and water, dried over magnesium sulphate and concentrated. The product crystallizes out with ether and is filtered off with suction.

Yield: 20.0 g (96.5% of theory)
Melting point: 101° C.
$R_f = 0.63$ (toluene:ethanol 3:1)
Thin layer chromatography, aluminum foil, silica gel 60
$F_{254}$, layer thickness 0.2 mm, Art. 5562 Merck The compounds listed in Table 1 were prepared analogously to the instructions of Example 4:

TABLE 1

Structure:
- Indole with NH—SO$_2$—R$^2$ on ethyl side chain
- N substituted with CH$_2$—CH$_2$—COOCH$_3$

| Example No. | R$^2$ | Melting point | R$_f$* |
|---|---|---|---|
| 5 | 4-Cl-phenyl | 93° C. | 0.68 |
| 6 | 3,4-diCl-phenyl | 105° C. | 0.71 |
| 7 | 4-Br-phenyl | 87° C. | 0.69 |
| 8 | phenyl | 96° C. | 0.67 |

*(Toluene/ethanol 3:1) Thin layer chromatography, aluminum foil, silica gel 60 F$_{254}$, layer thickness 0.2 mm, Art. 5562 Merck

Example 9

Methyl 2-bromo-3-[2-(4-toluylsulphonylamino)ethyl]-indole-1-propionate

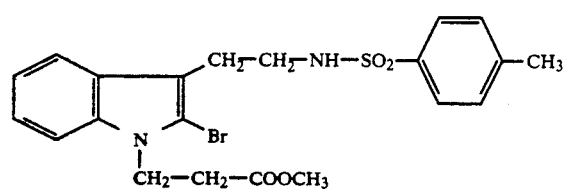

4.0 g (10 mmol) of the compound from Example 4 are dissolved in 250 ml of absolute methylene chloride. 1.6 g of bromine in 200 ml of absolute methylene chloride are added dropwise at −5° C. in the course of 45 minutes. When the addition has ended, the mixture is subsequently stirred at 0° C. for a further 30 minutes. The reaction mixture is washed twice with saturated sodium bicarbonate solution, dried over magnesium sulphate and concentrated on a rotary evaporator. Chromatography of the residue on silica gel using toluene:ethyl acetate (2:1) as the eluting agent gives a pale yellow resin.

Yield: 3.5 g (73.1% of theory)

R$_f$=0.69 (toluene:ethyl acetate 3:1)

Thin layer chromatography, aluminium foil, silica gel 60 F$_{254}$, layer thickness 0.2 mm, Art. 5562 Merck The compounds listed in Table 2 were prepared analogously to the instructions of Example 9:

TABLE 2

Structure:
- Indole with NH—SO$_2$—R$^2$ on ethyl side chain
- 2-position substituted with R$^3$
- N substituted with CH$_2$—CH$_2$—COOCH$_3$

| Example No. | R$^2$ | R$^3$ | Melting point | R$_f$* |
|---|---|---|---|---|
| 10 | 4-methylphenyl | Br | 93° C. | 0.70 |
| 11 | 4-Cl-phenyl | Br | 112° C. | 0.61 |
| 12 | 3,4-diCl-phenyl | Br | — | 0.72 |
| 13 | 4-Br-phenyl | Br | 122° C. | 0.68 |
| 14 | 4-Br-phenyl | Cl | 113° C. | 0.68 |
| 15 | 4-Cl-phenyl | Cl | 89° C. | 0.71 |
| 16 | 3,4-diCl-phenyl | Cl | — | 0.72 |

*(Toluene/ethanol 3:1) Thin layer chromatography, alumin foil, silica gel 60 F$_{254}$, layer thickness 0.2 mm, Art. 5562 Merck

Example 17

2-Bromo-3-[2-(4-toluylsulphonylamino)ethyl]-indole-1-propionic acid

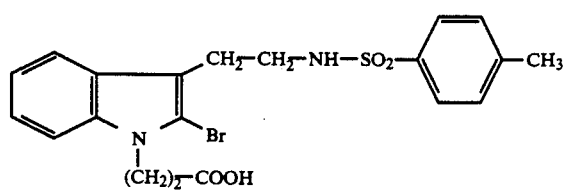

20 ml of 1 molar sodium hydroxide solution are added to a solution of 2.7 g (5.6 mmol) of the compound from Example 9 in 60 ml of 1,2-dimethoxyethane at 0° C. and the mixture is stirred at 0° C. for 30 minutes and then at room temperature for 1 hour. The aqueous phase is separated off and extracted twice with ether. The aqueous phase is then rendered acid with 1 molar hydrochloric acid, while cooling with ice. The oily product which has precipitated is extracted 3 times with methylene chloride and the combined organic phases are washed with water, dried over magnesium sulphate and concentrated on a rotary evaporator. The product crystallizes with a little toluene and is filtered off with suction.

Yield: 2.0 g (76.3% of theory)
Melting point: 118° C.
$R_f$=0.50 (toluene:ethanol 3:1)
Thin layer chromatography, aluminum foil, silica gel 60
$F_{254}$, layer thickness 0.2 mm, Art. 5562 Merck

Example 18
2-Bromo-3-[2-(4-fluoro-phenylsulphonylamino)ethyl]-indole-1-propionic acid

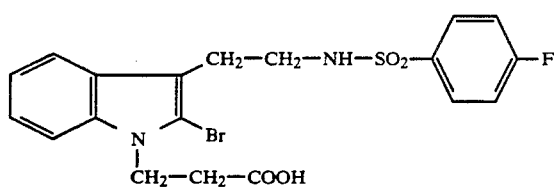

1.45 g (5 mmol) of N-{2-[1-(2-carboxyethyl)-1H-indol-3-yl]}ethyl-(4-fluoro-phenyl)-sulphonamide are dissolved in 100 ml of absolute methylene chloride, and 0.26 ml of bromine in 100 ml of methylene chloride are added dropwise at 0° C. in the course of 1 hour. The reaction mixture is stirred at 0° C. for a further hour and then concentrated on a rotary evaporator. Chromatography on silica gel using toluene/ethanol (6:1) as the eluting agent gives a pale yellow oil which is crystallized by a methylene chloride/ether mixture.

Yield: 303 mg (17.5% of theory)
Melting point: 131° C.
$R_f$=0.46
Thin layer chromatography, aluminum foil, silica gel 60
$F_{254}$, layer thickness 0.2 mm, Art. 5562 Merck The compounds listed in Table 3 were prepared analogously to the instructions of Examples 17 and 18.

TABLE 3

| Example No. | $R^2$ | $R^3$ | Melting point | $R_f$* |
|---|---|---|---|---|
| 19 | 3,4-dichlorophenyl | Br | 142° C. | 0.43 |
| 20 | 2,3,4-trichlorophenyl | Br | 169° C. | 0.37 |
| 21 | phenyl | Br | 115° C. | 0.54 |
| 22 | 4-chlorophenyl | Br | 126° C. | 0.40 |
| 23 | 4-bromophenyl | Br | 125° C. | 0.50 |
| 24 | 4-bromophenyl | Cl | 136° C. | 0.47 |
| 25 | 4-chlorophenyl | Cl | 165° C. | 0.53 |
| 26 | 3,4-dichlorophenyl | Cl | 160° C. | 0.55 |

*(Toluene/ethanol 3:1) Thin layer chromatography, aluminum foil, silica gel 60 $F_{254}$, layer thickness 0.2 mm, Art. 5562 Merck It is understood that the specification and examples are illustrative but not limitative of the present invention and that other embodiments within the spirit and scope of the invention will suggest themselves to those skilled in the art.

We claim:

1. A 2-halogen-substituted N-indolylethyl-sulphonamide of the formula

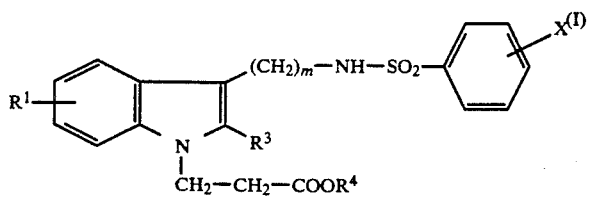

in which $R^1$ represents hydrogen, halogen or trifluoromethyl,
X is 0 to 5 halogen atoms, or is a member selected from the group consisting of cyano, trifluoromethyl, trifluoromethoxy, trifluoromethylthio, alkyl, alkoxy, alkoxycarbonyl and alkylthio having in each case up to 8 carbon atoms, hydroxyl, carboxyl, phenyl, phenoxy, benzyloxy and benzylthio, or is a group of the formula —NR$^6$R$^7$, wherein R$^6$ and R$^7$ are identical or different and denote hydrogen, straight-chain or branched alkyl having up to 8 carbon atoms, aryl having 6 to 10 carbon atoms or acetyl, R$^3$ represents halogen, R$^4$ represents hydrogen or straight-chain or branched alkyl having up to 8 carbon atoms, or represents phenyl and m represents one of the numbers 2, 3, or 4, or a pharmaceutically acceptable salt thereof.

2. A 2-halogen-substituted N-indolylethylsulphonamide or a salt thereof according to claim 1, wherein R$^1$ represents hydrogen, fluorine, chlorine, bromine or trifluoromethyl, X is 0 to 3 identical or different substituents selected from the group consisting of fluorine, chlorine and bromine, or is a member selected from the group consisting of cyano, trifluoromethyl, trifluoromethoxy, trifluoromethylthio, alkyl, alkoxy, alkoxycarbonyl and alkylthio having in each case up to 6 carbon atoms, hydroxyl, carboxyl, phenyl, phenoxy, benzyloxy and benzylthio or a group of the formula —NR$^6$R$^7$, wherein R$^6$ and R$^7$ are identical or different and denote hydrogen, straight-chain or branched alkyl having up to 6 carbon atoms, phenyl or acetyl, R$^3$ represents fluorine, chlorine, bromine or iodine, R$^4$ represents hydrogen or straight-chain or branched alkyl having up to 6 carbon atoms, or represents phenyl and m represents one of the numbers 2 or 3.

3. A 2-halogen-substituted N-indolylethyl-sulphonamide or salt thereof according to claim 1, wherein R$^1$ represents hydrogen, fluorine, chlorine or trifluoromethyl, X represents 0 to 3 identical or different substituents selected from the group consisting of fluorine, chlorine and bromine, or is a member selected from the group consisting of cyano, trifluoromethyl, trifluoromethoxy, trifluoromethylthio, methyl, ethyl, propyl, isopropyl, butyl, tert.-butyl, methoxy, ethoxy, methoxycarbonyl, ethoxycarbonyl, methylthio, ethylthio, hydroxyl, carboxyl, phenyl, phenoxy, benzyloxy and benzylthio, or is a group of the formula —NR$^6$R$^7$, wherein R$^6$ and R$^7$ are identical or different and denote hydrogen, methyl, ethyl or propyl, R$^3$ represents fluorine, chlorine or bromine, R$^4$ represents hydrogen, straight-chain or branched alkyl having up to 4 carbon atoms or phenyl and m represents the number 2.

4. A compound according to claim 1, wherein such compound is 2-bromo-3-[2-(4-fluoro-phenylsulphonylamino) ethyl]-indole-1-propionic acid of the formula

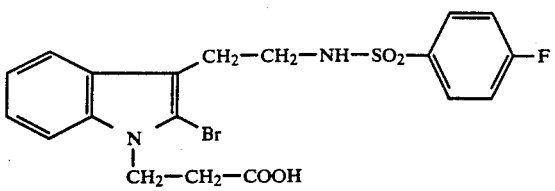

or a salt thereof.

5. A compound according to claim 1, wherein such compound is 2-bromo-3-[2-(phenylsulphonylamino)ethyl]-indole-1-propionic acid of the formula

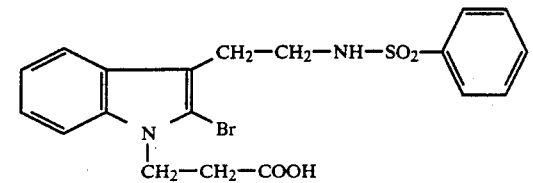

or a salt thereof.

6. A compound according to claim 1, wherein such compound is 2-bromo-3-[2-(4-chloro-phenylsulphonylamino) ethyl]-indole-1-propionic acid of the formula

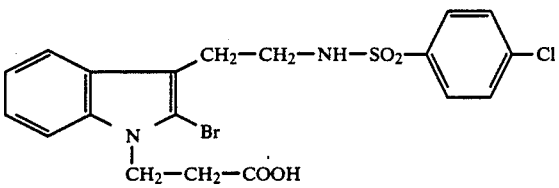

or a salt thereof.

7. A compound according to claim 1, wherein such compound is 2-chloro-3-[2-(4-chloro-phenylsulphonylamino) ethyl]-indole-1-propionic acid of the formula

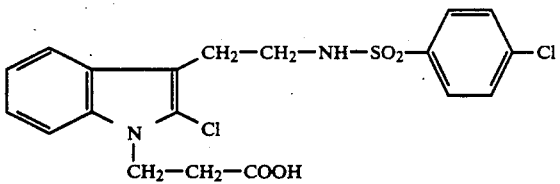

or a salt thereof.

8. A platelet agregation-inhibiting and thromboxane A$_2$-antagonizing composition comprising an amount effective therefor of a compound or salt thereof according to claim 1 and a diluent.

9. A unit dose of a composition according to claim 8 in the form of a tablet, capsule or ampoule.

10. A method of inhibiting aggregation of platelets in a patient in need thereof which comprises administering to such patient an amount effective therefor of a compound or salt thereof according to claim 1.

11. The method according to claim 10, wherein such compound is 2-bromo-3-[2-(4-fluoro-phenylsulphonylamino) ethyl]-indole-1-propionic acid, 2-bromo-3-[2-(phenylsulphonylamino)ethyl]-indole-1-propionic acid,
2-bromo-3-[2-(4-chloro-phenylsulphonylamino) ethyl-indole-1-propionic acid or
2-chloro-3-[2-(4-chloro-phenylsulphonylamino) ethyl]-indole-1-propionic acid, or a salt thereof.

12. A method of antagonizing thromboxane $A_2$ in a patient in need thereof which comprises administering to such patient an amount effective therefor of a compound or salt thereof according to claim 1.

13. The method according to claim 12, wherein such compound is
2-bromo-3-[2-(4-fluoro-phenylsulphonylamino) ethyl]-indole-1-propionic acid,
2-bromo-3-[2-(phenylsulphonylamino)ethyl]-indole-1-propionic acid,
2-bromo-3-[2-(4-chloro-phenylsulphonylamino) ethyl-indole-1-propionic acid or
2-chloro-3-[2-(4-chloro-phenylsulphonylamino) ethyl]-indole-1-propionic acid, or a salt thereof

* * * * *

UNITED STATES PATENT AND TRADEMARK OFFICE
CERTIFICATE OF CORRECTION

PATENT NO. : 5,015,657

DATED : May 14, 1991

INVENTOR(S) : Boshagen et al.

It is certified that error appears in the above-identified patent and that said Letters Patent is hereby corrected as shown below:

Title Page   ABSTRACT: Line 17 before " represents straight " insert -- $R^2$ --

Signed and Sealed this

Twenty-fifth Day of May, 1993

Attest:

MICHAEL K. KIRK

*Attesting Officer*   Acting Commissioner of Patents and Trademarks